(12) United States Patent  (10) Patent No.: US 7,947,667 B2
Stevenson et al.  (45) Date of Patent: May 24, 2011

(54) PROCESS AND INTERMEDIATES FOR THE PRODUCTION OF 7-SUBSTITUTED ANTIESTROGENS

(75) Inventors: Robert Stevenson, Cheshire (GB); Fraser Witton Kerr, Södertälje (SE); Anthony Raymond Lane, Cheshire (GB); Eve Joanne Brazier, Cheshire (GB); Phillip John Hogan, Cheshire (GB); David Dermot Patrick Laffan, Cheshire (GB)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 10/398,924

(22) PCT Filed: Oct. 9, 2001

(86) PCT No.: PCT/GB01/04485
§ 371 (c)(1),
(2), (4) Date: Sep. 11, 2003

(87) PCT Pub. No.: WO02/32922
PCT Pub. Date: Apr. 25, 2002

(65) Prior Publication Data
US 2005/0101583 A1   May 12, 2005

(30) Foreign Application Priority Data

Oct. 14, 2000  (GB) .................... 0025221.3

(51) Int. Cl.
*A61K 31/56* (2006.01)
*A61K 31/00* (2006.01)
*C07J 41/00* (2006.01)
(52) U.S. Cl. ......... 514/169; 514/170; 514/177; 552/558
(58) Field of Classification Search .................. 514/172, 514/178, 169, 170, 177; 552/590, 500, 558
See application file for complete search history.

(56) References Cited

U.S. PATENT DOCUMENTS

| 3,944,576 | A | * | 3/1976 | van den Broek et al. | ...... 552/617 |
| 4,659,516 | A | * | 4/1987 | Bowler et al. | ................ 514/144 |
| 5,211,831 | A | | 5/1993 | Vitale et al. | |
| 5,502,046 | A | | 3/1996 | Bohlmann et al. | |
| 5,595,985 | A | * | 1/1997 | Labrie | ........................ 514/169 |
| 5,952,319 | A | * | 9/1999 | Cook et al. | .................... 514/179 |
| 6,288,051 | B1 | * | 9/2001 | Bittler et al. | .................. 514/182 |
| 7,196,074 | B2 | * | 3/2007 | Blye et al. | ..................... 514/178 |
| 7,323,602 | B2 | * | 1/2008 | Warren et al. | ..................... 568/56 |

FOREIGN PATENT DOCUMENTS

EP    0 138 504 A2    4/1985
WO    93/06124 A1    4/1993

OTHER PUBLICATIONS

Bowler, J., et al., "Novel Steroidal Pure Antiestrogens," Steroids, 54(1):71-99 (1989).

Golob, T., et al., "Antiestrogenic Activities of 3,8-Dihydroxy-6,11-dihydrobenzo[a]carbazoles with Sulfur-Containing Side Chains," Arch. Pharm. Pharm. Med. Chem., 333:305-311 (2000).
Bowler, Jean et al., Novel Steroidal Pure Antiestrogens, Steroids, Jul. 1989, pp. 71-99, vol. 54/1.
Modi, Sandeep P. et al., Conjugate Addition of Grignard Reagants to Enones and Dienones, 1989, pp. 2317-2321, vol. 54.
Rao, Pemmaraju, N., et al., Preparative Chemical Methods for aromatization of 19-nor-delta4-3-oxosteroids, Steroids, Nov. 1994, pp. 621-627, vol. 59.
Wakeling AE, et al. Therapeutic Potential of Pure Antioestrogens in the Treatment of Breast Cancer, Steroid Biochemistry, 1990c, vol. 37, pp. 771-775.
Wakeling AE, et al., Steroidal Pure Antioestrogen, J. Endocrinology 1987, vol. 112: pp. R7-R10.
Wakeling AE, et al., Biology and Mode of Action of Pure Antioestrogens, J. Steroid Biochemistry, 1988, vol. 30 No. 1-6, 141-147.
Howell et al., Response to a specific antioestrogen (ICI 182780) in tarmoxifen-resistant breast cancer, The Lancet, Jan. 7, 1995, vol. 345, pp. 29-30.

* cited by examiner

*Primary Examiner* — Sabiha Qazi

(57) ABSTRACT

A process for preparing an intermediate compound of formula (II)

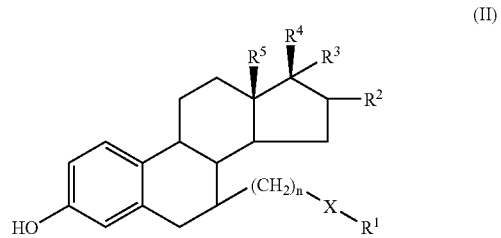

(II)

where X is as defined in the specification, $R^1$ is haloalkyl, alkyl, alkenyl, cycloalkyl, carboxyalkyl, alkoxycarbonylalkyl, aryl or arylalkyl;
$R^2$, $R^3$, $R^4$ and $R^5$ are organic groups as defined in the specification, which process comprises aromatisation of a compound of formula (III)

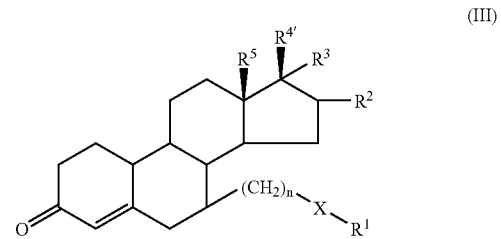

(III)

where $R^1$, $R^2$, $R^3$, n, X and $R^5$ are as defined in relation to formula (II) and $R^{4'}$ is a group $R^4$ or a precursor group thereof, and thereafter if necessary or desired, carrying out one or more of the following steps: (i) removing any hydroxy-protecting groups R; (ii) converting a precursor group $R^{4'}$ to a group $R^4$, or where $R^{4'}$ is a group $R^4$, converting it to a different such group.
Compounds obtained are useful intermediates for example in the preparation of fulvestrant. Novel intermediates are also claimed.

5 Claims, No Drawings

PROCESS AND INTERMEDIATES FOR THE PRODUCTION OF 7-SUBSTITUTED ANTIESTROGENS

This application is a national stage filing under 35 U.S.C. 371 of International Application No. PCT/GB01/04485, filed Oct. 9, 2001, which claims priority from United Kingdom Patent Application No. 0025221.3, filed Oct. 14, 2000, the specifications of each of which are incorporated by reference herein. International Application No. PCT/GB01/04485 was published under PCT Article 21(2) in English.

The invention relates to a new processes useful in the preparation of pharmaceutical compounds such as fulvestrant, and to novel intermediates for use in the process.

U.S. Pat. No. 4,659,516 describes a group of steroid derivatives, which have antioestrogenic activity.

Fulvestrant (Faslodex™, ZD9238, ICI 182,780) (Wakeling A E. J. Steroid Biochemistry 1990c; 37: 771-5, Wakeling A E, et al. J. Endocrinology 1987; 112: R7-10 and Wakeling A E et al. J. Steroid Biochemistry 1988; 3: 141-7) is a particular example of such a steroidal derivative and is the first in a new class of potent pure antioestrogens which is completely free of the partial agonist, oestrogen-like activity, associated with currently available antioestrogens like tamoxifen.

Fulvestrant has already demonstrated efficacy in a phase II trial in women whose breast cancer has progressed following tamoxifen therapy (Howell et al., The Lancet, 1995, 345. 29-30). Fulvestrant has a novel mechanism of action, described as an estrogen receptor downregulator, with clear evidence of anti-tumour activity in advanced breast cancer.

The chemical name for fulvestrant is 7-alpha-[9-(4,4,5,5,5-pentafluoropentylsulphinyl)nonyl]-estra-1,3,5(10)-triene-3,17β-diol, and this is represented as formula (I).

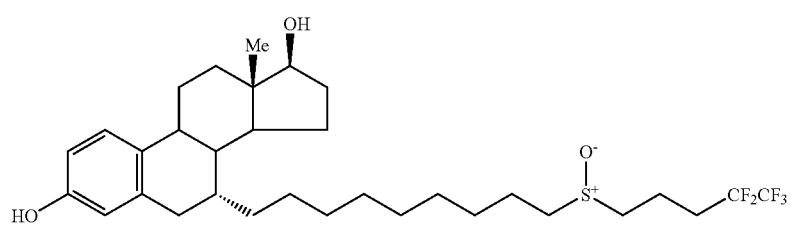

In U.S. Pat. No. 4,659,516, column 4 et seq., a general process route is described for the preparation of compounds of a similar type to fulvestrant. A summary of the general process as it would apply to the preparation of fulvestrant is described in Scheme 1. A process route is also described in Bowler J. (co-inventor of U.S. Pat. No. 4,659,516) Steroids (1989) 71-99 which is a similar route to that shown Scheme 1 hereinafter.

The applicants have found in particular, improved routes to these compounds.

According to the present invention there is provided a process for preparing an intermediate compound of formula (II),

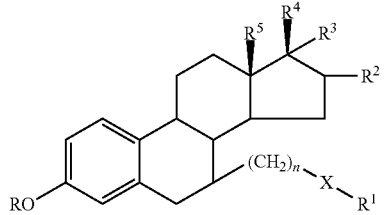

where X is S, SO, $SO_2$, O, $NR^6$, $N(O)R^6$, $(PO)R^6$, $NR^7$, COO—, $NR^7SO_2$, $CONR^6$, $CSNR^6$, $NR^7CO$, $NR^7C(NR^8)$ $NR^6$, $NR^7CS$, $NR^7CONR^6$, $SO_2NR^6$ or CO, where $R^6$ is hydrogen or $C_{1-6}$alkyl, $R^7$ is hydrogen or $C_{1-6}$alkyl and $R^8$ is cyano, hydrogen or nitro, n is an integer of from 3 to 14;

R is hydrogen or a hydroxy protecting group, $R^1$ is halo$C_{1-10}$alkyl, $C_{1-10}$alkyl, $C_{2-10}$alkenyl, $C_{2-10}$cycloalkyl, carboxy$C_{1-10}$alkyl, $C_{1-10}$alkoxycarbonyl$C_{1-10}$alkyl, aryl (such as phenyl), aryl($C_{1-10}$)alkyl (such as phenyl($C_{1-10}$) alkyl) or di($C_{1-6}$alkyl)amino;

$R^2$ is hydrogen, $C_{1-6}$alkyl or hydroxy, $R^3$ is hydrogen, $C_{1-6}$alkyl, $C_{2-6}$alkenyl or $C_{2-6}$alkynyl;

$R^4$ is hydroxy, $C_{1-10}$alkanoyloxy, carboxy$C_{1-10}$alkanoyloxy or aroyloxy (such as benzoyloxy);

$R^5$ is $C_{1-6}$alkyl; which process comprises aromatisation of a compound of formula (III)

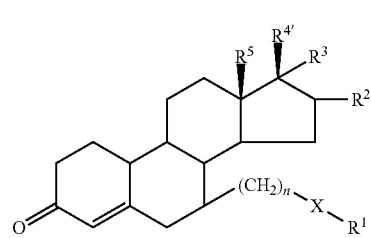

where $R^1$, $R^2$, $R^3$, n, X and $R^5$ are as defined in relation to formula (II) and $R^{4'}$ is a group $R^4$ or a precursor group thereof, and thereafter if necessary or desired, carrying out one or more of the following steps:
(i) removing any hydroxy protecting groups R;
(ii) converting a precursor group $R^{4'}$ to a group $R^4$, or where $R^{4'}$ is a group $R^4$, converting it to a different such group.

In particular, $R^{4'}$ is a group $OR^{10}$ where $R^{10}$ is a protecting group, for example a hydroxy protecting group such as acyloxy, in particular acetyloxy. In this case, removal of the protecting group using conventional methods such as those described in Protective Groups in Organic Synthesis, 2nd Edition, by Green et al., published by John Wiley & Sons. In particular deprotection, for example by hydrolysis, preferably alkaline hydrolysis, with a base such as an alkali metal hydroxide, will yield a compound of formula (II) where $R^{17}$ is hydroxy.

Aromatisation of the compound of formula (III) may be effected by various conventional methods, such as those described in Steroids (1989) 71-99 and Steroids (1994) 621-627. In a particularly preferred embodiment, the reaction is effected using a copper salt such as cupric bromide. Most preferably the reaction is effected in the presence of an acylating agent such as an acid anhydride, for example acetic anhydride. The copper salt, and preferably also acetic anhydride, is suitably added to a solution of a compound of formula (III) in an organic solvent such as acetonitrile, at moderate temperatures for example from about 0°-40° C. and conveniently at about 20° C. Suitably, a salt, in particular an alkali metal halide such as lithium bromide, are added at the same time, in order to assist in the solubilisation of the copper salt and thus reduce the amount of solvent required.

The use of an acetylating agent such as acetic anhydride in the aromatisation step has been found to protect the phenol in situ and prevent the formation of halogenated impurities, in particular 2-halo impurities such as the 2-bromo impurities of formula (A).

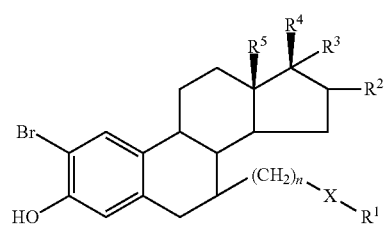

(A)

This is probably a result of the fact that acetyloxy groups are produced instead of hydroxy groups in the intermediate. For example, the following 2-Br impurity, was found to occur using the prior published route to fulvestrant.

This impurity was found to be very difficult to remove by crystallisation in the purification of fulvestrant. By using acetic anhydride in the process the formation of this product is largely eliminated.

Furthermore, by using an acetylating agent in the reaction, the product of the aromatisation reaction is a compound of formula (II) where R is acetyl. This may conveniently be removed in optional step (i), which, where $R^{12}$ is also an acyl group such as acetyl, may be combined with step (ii) in a single reaction.

In a further preferred embodiment, thiourea is added subsequent to the aromatisation reaction to precipitate copper waste from the reaction mixture prior to the deacetylation step.

Thus in a further embodiment, the invention provides a method of preparing a compound of formula (XIII).

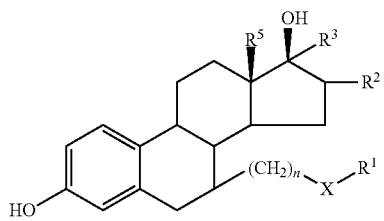

(XIII)

where X, n, $R^1$, $R^2$, $R^3$ and $R^5$ are as defined in relation to formula (II), by reacting a compound of formula (XIV)

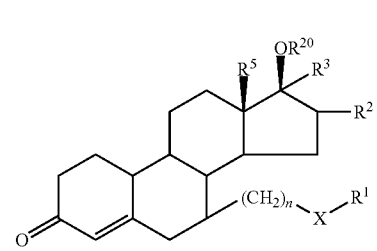

(XIV)

where X, n, $R^1$, $R^2$, $R^3$ and $R^5$ are as defined in relation to formula (II), and $R^{20}$ is hydrogen or a protecting group, in particular an acetyl group, with a copper salt in the presence of an acetic anhydride, and then hydrolysing the thus formed acetyloxy groups.

A particular compound of formula (II) which can be prepared by the method of the invention is an intermediate used in the preparation of fulvestrant of formula (I). Such a compound is a compound of formula (IIA).

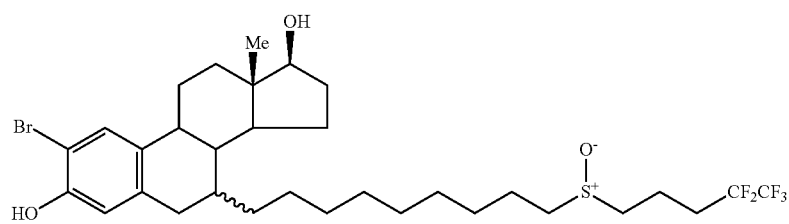

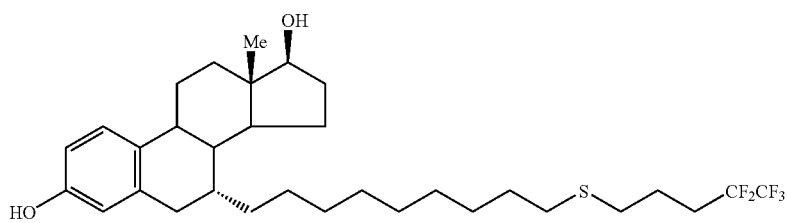
(IIA)

Compounds of formula (III) are novel intermediates and form a further aspect of the invention.

These compounds are suitably prepared by reacting a compound of formula (IV)

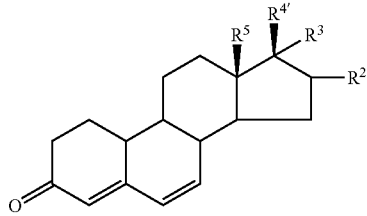
(IV)

where $R^2$, $R^3$ and $R^5$ are as defined in relation to formula (II), and $R^{4'}$ is as defined in relation to formula (III), with a compound of formula (V)

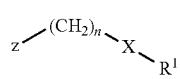
(V)

where n, X and $R^1$ are as defined in relation to formula (II) and Z is a leaving group.

Suitable leaving groups Z are conventional groups such as halo, mesylate and tosylate, but in a particularly preferred embodiment, Z is a metal halide of formula $R^{11}$-M where M is a metal ion and $R^{11}$ is a halogen atom.

Preferably M is selected from magnesium, zinc, aluminium and titanium. A preferred metal atom M is magnesium.

Preferably $R^{11}$ is selected from chlorine, bromine and iodine. A preferred halo $R^{11}$ is bromine. Thus, in a preferred embodiment, the compound of formula (V) is an organometallic reagent and in particular is a Grignard reagent.

The coupling reaction between the organometallic reagent (V) and a compound of formula (IV) is promoted by the addition of a cuprous salt, such as a halide or cyanide (where preferably the salt is a chloride), optionally complexed with a ligand containing sulphur or phosphorus, all dissolved in a suitable solvent.

In a particular embodiment, it has been found that only catalytic amounts of the cuprous salt, for example less than 0.01 mol equivalents, are necessary. A suitable solvent is an ether, preferably tetrahydrofuran.

Using this reaction, it has been found that there is a greater preponderance of a preferred isomeric form of the compound of formula (III). Specifically, the bond indicated by an asterisk in the following copy of formula (III) may be in two stereochemical orientations giving rise to an α and a β form of the product.

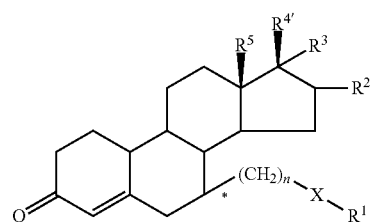
(III)

It has been found, in particular in the case of fulvestrant that the a form is preferred. The previously published route to this compound resulted in a mixture of α/β forms of about 1.9:1, whereas using an organometallic compound of formula (V) as described above, higher levels of the preferred α form, for example in a ratio of α/β of 2.5:1 are achievable.

Where the compound of formula (V) is an organometallic reagent, it is conveniently formed by the addition of element metal M to the alkyl halide of formula (VI),

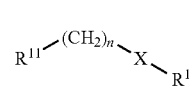
(VI)

wherein n, $R^1$ and X are as defined in relation to formula (II) and $R^{11}$ is as defined above in relation to formula (V), in a suitable solvent, such as tetrahydrofuran or ether.

Compounds of formula (V) where Z is a leaving group and compounds of formula (VI) are either known compounds (see for example WO93/06124 Example 4c) or they can be prepared from known compounds by conventional methods.

The reaction between compounds of formula (IV) and (V), is a novel method and forms a further aspect of the invention.

In particular in the above compounds (II), (III), (IV), (V) and (VI), $R^1$ is a haloalkyl group and in particular is a group of formula —$(CH_2)_3CF_2CF_3$.

Suitable examples of $R^2$ are hydrogen or $C_{1-3}$alkyl, but preferably hydrogen.

Preferably, $R^3$ is hydrogen.

A particular example of a suitable group $R^4$ is hydroxy or alkanoyloxy such as acetoxy. In particular in these compounds $R^4$ is hydroxy and $R^{4'}$ is acetoxy.

Suitably $R^5$ is a $C_{1-3}$alkyl group, and in particular methyl.

In these compounds also, n is preferably 9.

Preferred groups X are S, SO or $SO_2$. For the purposes of the present application however, a particularly preferred group X is S.

Compounds of formula (II) are therapeutic steroid derivatives, or intermediates used in the preparation of such compounds. In particular, compounds of formula (II) where X is S may be oxidised, in particular using oxidising agents such as hydrogen peroxide or periodate, to convert the group X to a group SO, and thereafter subject to further purification as necessary. The products may be obtained in the form of free compounds, pharmaceutically-acceptable salts thereof, esters thereof or any possible solvates of either of these.

The methods and intermediates of the invention form a new economical route for the preparation of certain steroid derivatives, including fulvestrant. This route for the preparation of fulvestrant is conveniently summarised in Scheme 2 hereinafter.

The Scheme 1 route has the following disadvantages when compared to the Scheme 2 route:
1. There are seven steps from the expensive "dienone" intermediate.
2. There are no crystalline intermediates between the starting material and the final product. Therefore, isolation and purification between steps is difficult.
3. The yield is low—needing approximately a ratio by weight of 11 of dienone to produce 1 of fulvestrant.
4. The step of adding the side chain to the 7 position of the dienone steroid is favourable to the preferred α position compared to the unwanted β position at a ratio of 1.9:1.

The process of Scheme 2 offers several advantages when compared to the process of Scheme 1.
1. There are only four steps from the dienone intermediate.
2. Although in the case of fulvestrant, none of the intermediates can be crystallised, making isolation and purification difficult, the whole reaction can be carried out in solution until the final product is obtained which can be crystallised out of solution.
3. The yield is greatly improved—needing approximately a ratio by weight of 2 of dienone to produce 1 of fulvestrant.
4. The α/β ratio is improved to about 2.5:1.

The unwanted β form of fulvestrant is removed after the oxidation step as the final step prior to purification by recrystallisation.

In a particular embodiment, the process of the invention is used to produce a compound of formula (IIA) as defined above, by reacting a compound of formula (VIII) as defined below, and removal of the protecting group $R^{12}$. Suitably in this case, $R^{12}$ is acetyl and is removed by alkaline hydrolysis.

Therefore in a further aspect, the invention provides a process for the preparation of fulvestrant which comprises coupling a compound of formula (VII)

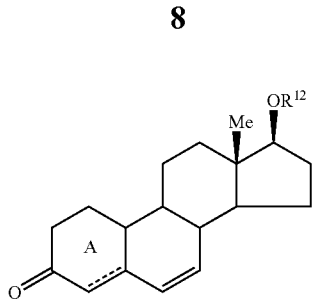

wherein $R^{12}$ is a protecting group, with a compound of formula (X),

L$\diagdown\diagdown\diagdown\diagdown\diagdown\diagdown\diagdown$S$\diagdown\diagdown$CF$_2$CF$_3$ (X)

wherein L is a suitable leaving group, and to the product formed performing the following three steps
(1) aromatisation of the A-ring
(2) removing protecting group $R^{12}$
(3) oxidation of the sulphide to the sulphoxide to form fulvestrant.

In particular L is a leaving group Z as defined above in relation to formula (V).

Preferred protecting groups $R^{12}$ are acyl groups such as acetyl.

As described above, the aromatisation of the A-ring is suitably effected in the presence of an acetylating agent such as acetic anhydride. This protects the phenol ring in situ, and furthermore, produces yields an intermediate of formula (IX)

(IX)

wherein R is acetyl and $R^{12}$ is as defined above. The group R may then be removed simultaneously with the group $R^{12}$ in step (2) in particular where the latter is acetyl.

The oxidation step may also be performed by the skilled reader according to known techniques. Care should be taken in the choice of reagents and conditions used to avoid formation of the sulphone. Any agent known in the art for the oxidation of sulphide to sulphoxide may be used, for example, hydrogen peroxide, a peracid (such as periodate or 3-chloroperoxybenzoic or peroxyacetic acid), gaseous oxygen in the presence of platinum or halogens and sources of positive halogen such as sodium hypochlorite and cerium IV salts. The oxidation is generally carried out under as mild conditions as possible in order to reduce the risk of over oxidation. In a preferred process, 2.0 mole equivalents of hydrogen peroxide are used.

A further particular feature of the invention is a process for the preparation of a compound of formula (VIII),

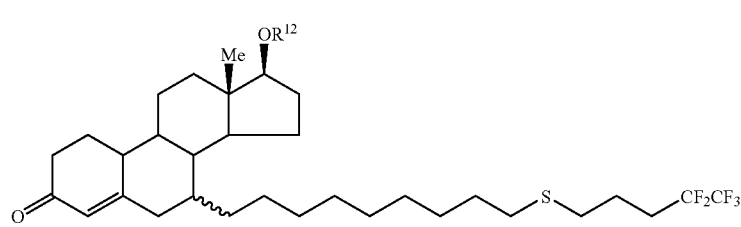

(VIII)

wherein $R^{12}$ is a protecting group, comprising coupling a compound of formula, (VII)

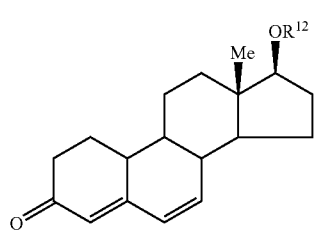

(VII)

wherein $R^{12}$ is a protecting group, with a compound of formula X,

(X)

wherein L is a suitable leaving group, as described above.

In particular, the compound of formula (X) is a compound of formula (XI)

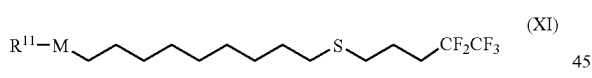

(XI)

wherein M is a metal atom and $R^{11}$ is a halo atom. The reaction is suitably carried out as described above in relation to the reaction between compounds of formula (IV) and (V). Thus, preferably M is selected from magnesium, zinc, aluminium and titanium. A preferred metal atom M is magnesium. Preferably $R^{11}$ is selected from chlorine, bromine and iodine. A preferred halo $R^{11}$ is bromine. Preferably the organometallic reagent is a Grignard reagent.

The coupling reaction between the organometallic reagent of formula (XI) and a compound of formula IX is promoted by the addition of a cuprous salt, such as a halide or cyanide (where preferably the salt is a chloride), optionally complexed with a ligand containing sulphur or phosphorus, all dissolved in a suitable solvent. It has been found that only catalytic amounts of the cuprous salt are necessary.

A suitable solvent is an ether, preferably tetrahydrofuran.

The organometallic reagent (XI) is conveniently formed by the addition of element metal M to the alkyl halide of formula (XII)

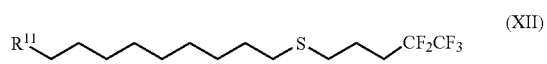

(XII)

wherein $R^{11}$ is as defined above, in a suitable solvent, such as tetrahydrofuran or ether.

The invention further provides a process for the preparation of fulvestrant, or a pharmaceutically acceptable salt or ester thereof, or a hydrate of any of these, which comprises (a) coupling a compound of formula (IX) as defined above, with a compound of formula (XI) as defined above; by the addition of a cuprous salt; all being dissolved in a suitable solvent to form a product of formula (VIII)

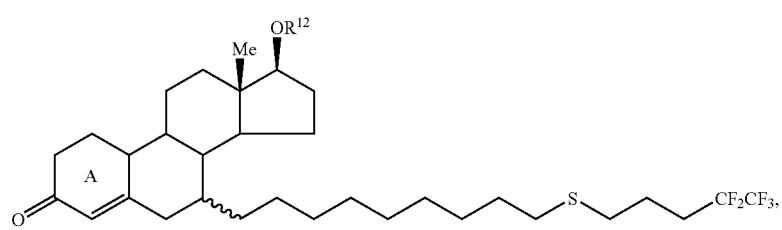

(VIII)

(b) aromatisation of the A-ring;
(c) removing protecting group $R^{12}$ and
(d) oxidising the sulphide group to sulphoxide to form fulvestrant.

Yet a further specific embodiment involves an aromatisation and deacetylation to produce fulvestrant intermediates. In particular, it comprises a method of preparing a compound of formula (XIIIA)

(XIIIA)

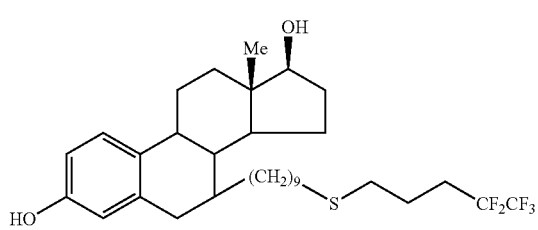

by reacting a compound of formula (XIVA)

(XIVA)

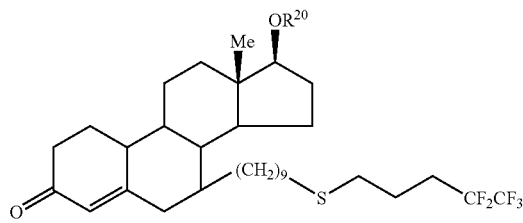

where $R^{20}$ is hydrogen or a protecting group, in particular an acetyl group, with a copper salt in the presence of an acetic anhydride, and then hydrolysing the thus formed acetyloxy groups.

The invention is illustrated by the following non-limiting examples, wherein notations such as EAS and PHS are as shown Scheme 2 hereinafter.

EXAMPLE 1

Preparation of Grignard Initiator

The terms relative volume and relative weight refer to the weight of Bromide. Bromide (0.2 mol equivalents) is added to magnesium raspings (1.15 mol equivalents) and tetrahydrofuran (2.0 relative volumes), then iodine (0.001 relative weight) is added to initiate the reaction. The mixture is diluted with more tetrahydrofuran (2.75 relative volumes) and the temperature is raised to about 45° C. More Bromide (0.8 mol equivalent) is added in several portions. The mixture is cooled, excess magnesium is allowed to settle out and the solution of Grignard reagent initiator is decanted prior to use in the next stage.

EXAMPLE 2

Preparation of Fulvestrant EAS

The term relative volume refers to the weight of Dienone.

To a solution of Grignard reagent initiator (about 0.05 mol equivalent) maintained under a nitrogen atmosphere are added magnesium raspings (2.19 mol equivalents) and tetrahydrofuran (8.4 relative volumes) and the mixture is heated to about 45° C. Bromide (0.247 mol equivalent) is added to initiate the reaction, then the mixture is diluted with tetrahydrofuran (2.2 relative volumes) and more Bromide (1.54 mol equivalents) is added in several portions, maintaining the temperature at about 45° C. The mixture is cooled and excess magnesium is allowed to settle out. To initiate subsequent batches of Grignard reagent, 17% of the solution is retained and the remaining 83% of the solution is decanted for use in the next stage.

The solution of Grignard reagent (1.35 mol equivalents) in tetrahydrofuran is diluted with more tetrahydrofuran (2.1 relative volumes) and cooled to −34° C. Cuprous chloride (0.078 mol equivalent) is added, followed by a solution of Dienone (1.00 mol equivalent) in tetrahydrofuran (4.7 relative volumes). The reaction is quenched with a solution of acetic acid (4.47 mol equivalents) in tetrahydrofuran (1.3 relative volumes) and the mixture is warmed to 20° C., then diluted with water (7.0 relative volumes). Tetrahydrofuran is removed by distillation and, after the addition of more water (3.0 relative volumes), the product is extracted into isohexane (5.0 relative volumes). The organic phase is separated and washed with 25% w/v aqueous potassium chloride (4.9 relative volumes). The solution of Fulvestrant EAS in isohexane thereby obtained is suitable for use directly in the next stage. The yield of Fulvestrant EAS is in the range 90-95%.

EXAMPLE 3

Preparation of Fulvestrant PHS

The term relative volume refers to the weight of Fulvestrant EAS.

Isohexane is distilled from the solution of Fulvestrant EAS (nominally 1.00 mol equivalent) and replaced by acetonitrile (3.0 relative volumes). A solution of cupric bromide (2.36 mol equivalents), lithium bromide (1.66 mol equivalents) and acetic anhydride (1.15 mol equivalents) in acetonitrile (3.0 relative volumes) is added over about three hours, maintaining the temperature at about 20° C. A further portion of acetic anhydride (0.85 mol equivalent) is added and after four hours the solution is poured into a mixture of thiourea (3.78 mol equivalents), toluene (3.0 relative volumes) and water (5.0 relative volumes) cooled to below 110° C. The pH of the mixture is adjusted to about 3 by the addition of dipotassium hydrogen phosphate (2.20 mol equivalents) and the precipitated copper complex is removed by filtration. The filter cake is washed with toluene (4.0 relative volumes) and the toluene solution containing Fulvestrant Acetyl PAS is washed three times with 10% w/v sodium chloride solution (3.0 relative volumes) at about 60° C. The toluene is removed by distillation and replaced by methanol (3.0 relative volumes). 47% w/w Sodium hydroxide solution (2.80 mol equivalents) is added and the mixture is held at 30° C. for five hours. At the end of the hydrolysis, the aqueous methanolic solution is extracted three times with isohexane (2.7 relative volumes) and neutralised with acetic acid (2.37 mol equivalents). Methanol is removed by distillation and the residue is partitioned between water (1.3 relative volumes) and ethyl acetate (4.0 relative volumes). The organic phase is concentrated by distillation to provide fulvestrant PHS as an approximately 50% w/w solution in ethyl acetate which is suitable for use directly in the next stage. The yield of Fulvestrant PHS is in the range 80-85%).

EXAMPLE 4

Preparation of Fulvestrant

The term relative volume refers to the weight of Fulvestrant PHS.

The solution of Fulvestrant PHS (nominally 1.00 mol equivalent) in ethyl acetate is diluted with ethyl acetate (2.5 relative volumes). Acetic acid (6.00 mol equivalents) is added, followed by 17% w/v aqueous hydrogen peroxide (2.00 mol equivalents) and the mixture is stirred at 23° C. for 8 hours. A further portion of ethyl acetate (2.0 relative volumes) is added and excess hydrogen peroxide is destroyed with a solution of sodium sulphite (1.50 mol equivalents) in water (3.5 relative volumes). The mixture is neutralised with dilute aqueous sodium hydroxide (6.30 mol equivalents) and the organic phase is separated off and washed with water (2.0 relative volumes). The ethyl acetate solution is dried and concentrated by distillation (to about 2.5 relative volumes), then cooled to 10° C. with seeding to promote crystallisation. The solid is filtered off and washed with cold ethyl acetate (1.0 relative volume). Further crystallisations from ethyl acetate (about 2.5 relative volumes) are carried out to achieve the required purity. The overall yield of Fulvestrant from Dienone is about 30%.

Scheme 1

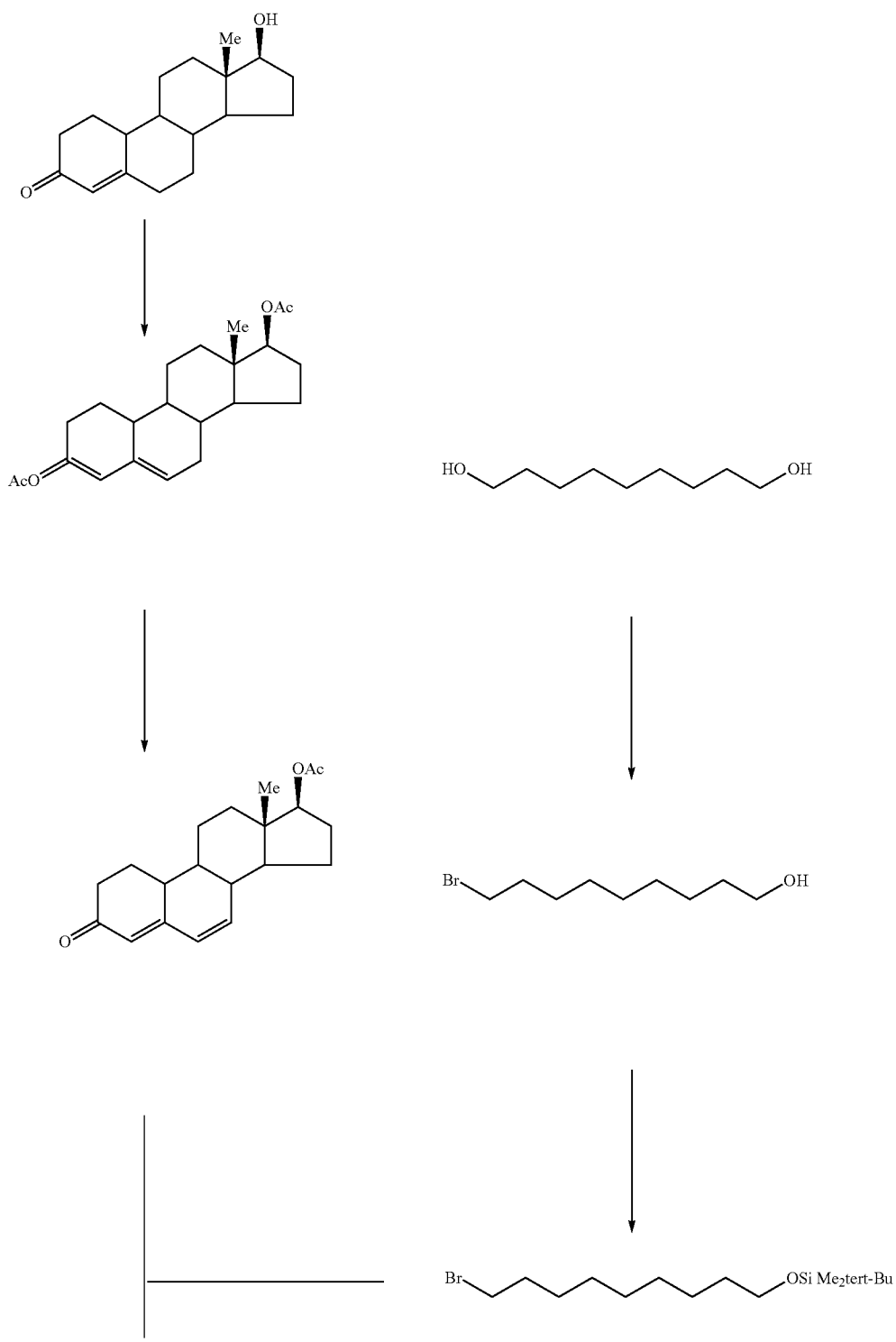

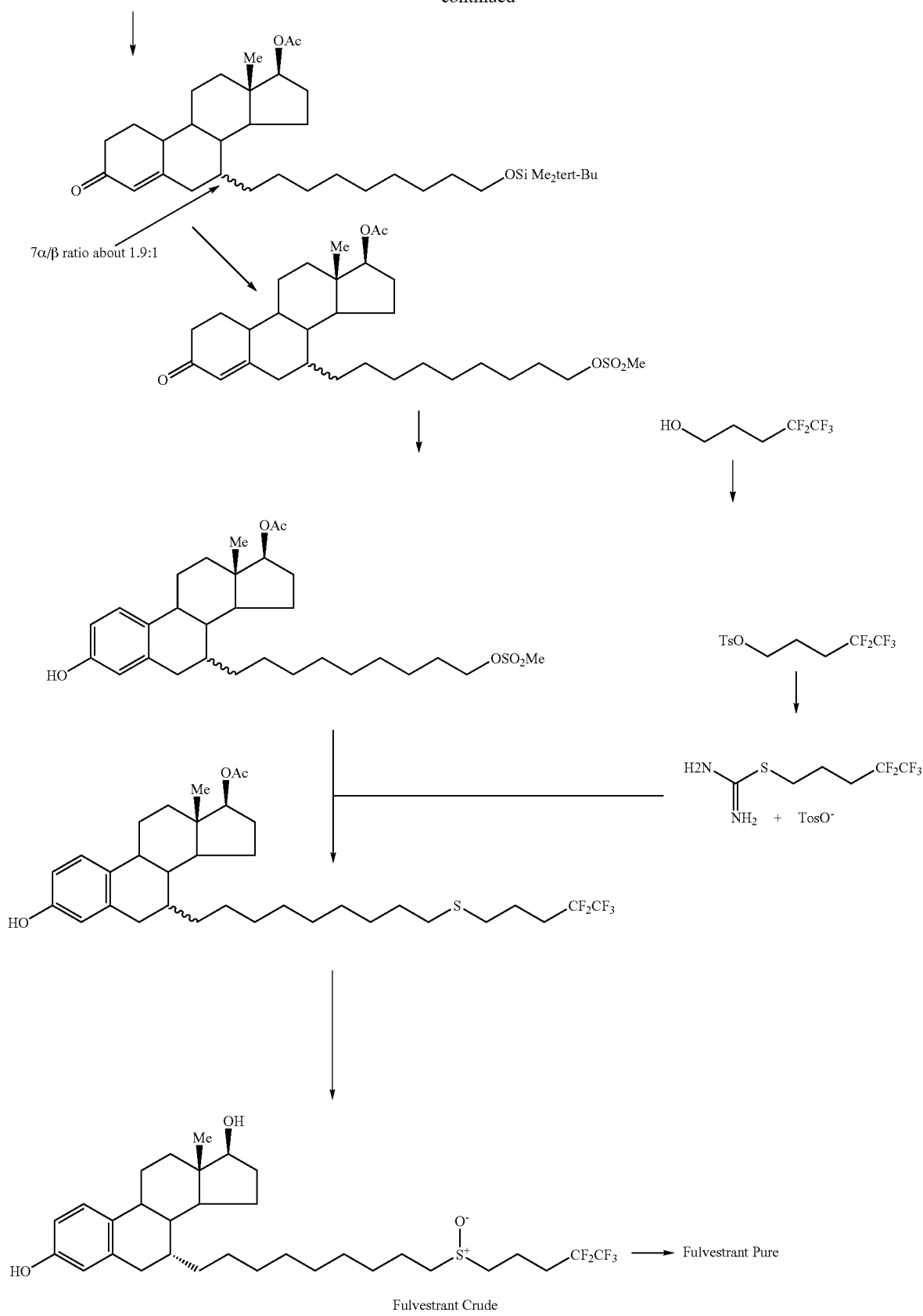
-continued
Fulvestrant Crude → Fulvestrant Pure

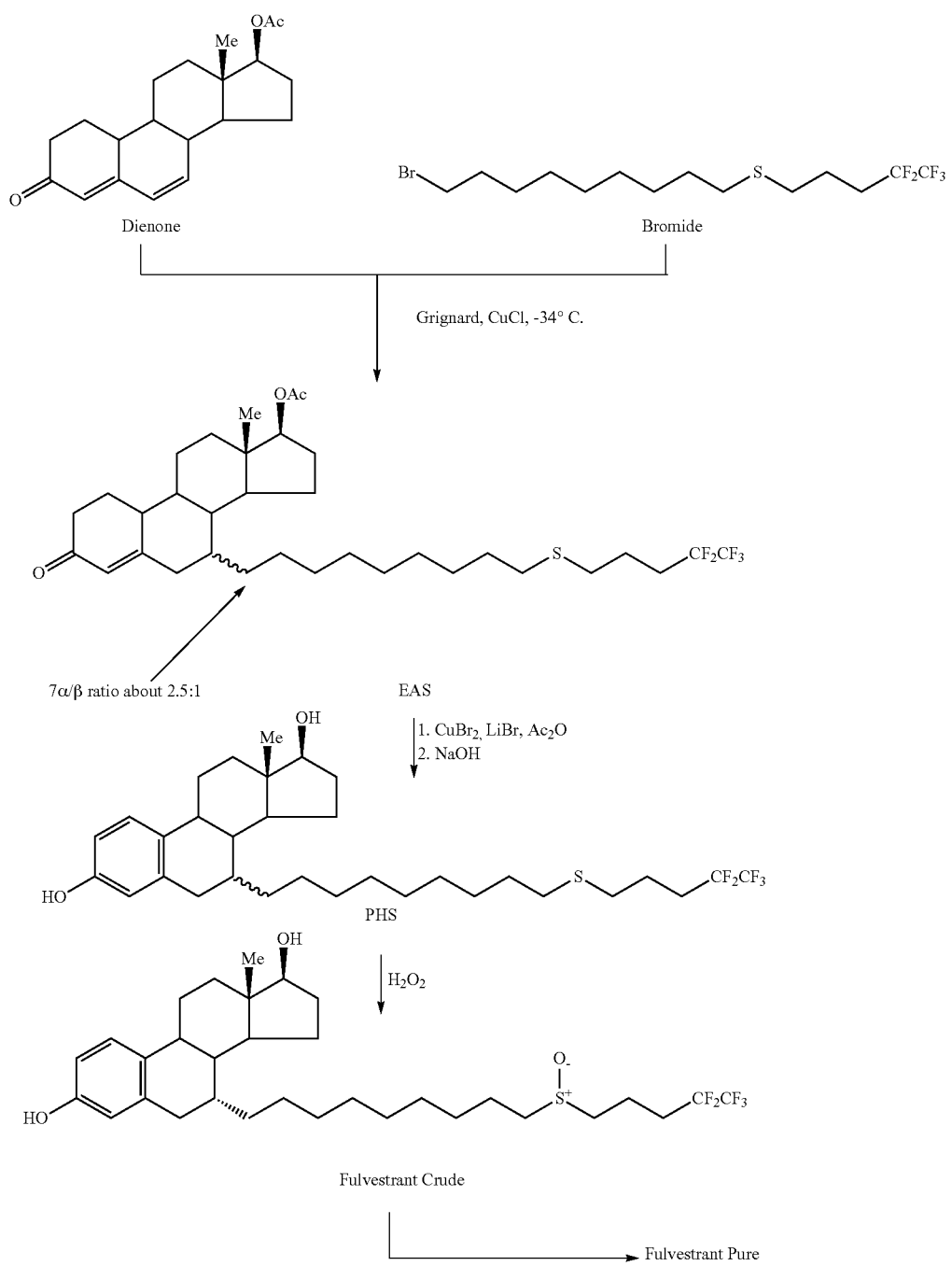

Scheme 2

The invention claimed is:
1. A method of preparing a fulvestrant composition while largely eliminating a 2-bromo impurity comprising:
aromatizing 3-oxo-7-{9-[(4,4,5,5,5-pentafluoropentyl)sulfanyl]nonyl}estr-4-3n-17-yl acetate in the presence of an acylating agent under conditions such that 7-{9-[(4,4,5,5,5-pentafluoropentyl)sulfanyl]nonyl}estr-1,3,5(10)triene-3-17-diyl diacetate is formed;
reacting 7-{9-[(4,4,5,5,5-pentafluoropentyl)sulfanyl]nonyl}estr-1,3,5(10)triene-3-17-diyl diacetate and a base under conditions such that 7-{9-[(4,4,5,5,5-pentafluoropentyl)sulfanyl]nonyl}estr-1,3,5(10)triene-3-17-diol is formed;
reacting 7-{9-[(4,4,5,5,5-pentafluoropentyl)sulfanyl]nonyl}estr-1,3,5(10)triene-3-17-diol and an oxidizing agent under conditions such that a fulvestrant composition if formed; and
purifying said fulvestrant composition by crystallization.

2. The method of claim 1, wherein aromatizing is reacting 3-oxo-7-{9-[(4,4,5,5,5-pentafluoropentyl)sulfanyl]nonyl}estr-4-3n-17-yl acetate with cupric bromide, lithium bromide, and said acylating agent in acetonitrile.

3. The method of claim 2, wherein said acylating agent is acetic anhydride.

4. The method of claim 1, wherein said base is sodium hydroxide.

5. The method of claim 1, wherein the oxidizing agent is hydrogen peroxide.

* * * * *